US009688623B2

(12) United States Patent
Venkateswaralu et al.

(10) Patent No.: US 9,688,623 B2
(45) Date of Patent: Jun. 27, 2017

(54) PROCESSES FOR THE PREPARATION OF (S)-1-(3-ETHOXY-4-METHOXYPHENYL)-2-METHANESULFONYLETHYLAMINE

(71) Applicant: CELGENE CORPORATION, Summit, NJ (US)

(72) Inventors: Jasti Venkateswaralu, Hyderabad (IN); Chinnapillai Rajendiran, Hyderabad (IN); Nallamaddi Ravikumar Reddy, Hyderabad (IN); Terrence Joseph Connolly, Warwick, NY (US); Alexander L. Ruchelman, Cream Ridge, NJ (US); Jeffrey Eckert, Hazlet, NJ (US); Anthony Joseph Frank, Easton, PA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/414,782

(22) Filed: Jan. 25, 2017

(65) Prior Publication Data
US 2017/0129852 A1 May 11, 2017

Related U.S. Application Data

(62) Division of application No. 14/882,564, filed on Oct. 14, 2015, now Pat. No. 9,586,897, which is a division of application No. 13/771,164, filed on Feb. 20, 2013, now Pat. No. 9,187,417.

(60) Provisional application No. 61/601,226, filed on Feb. 21, 2012.

(51) Int. Cl.
  *C07C 317/28* (2006.01)
(52) U.S. Cl.
  CPC ........ *C07C 317/28* (2013.01); *C07B 2200/07* (2013.01)
(58) Field of Classification Search
  None
  See application file for complete search history.

(56) References Cited

U.S. PATENT DOCUMENTS

| | | | |
|---|---|---|---|
| 6,011,050 | A | 1/2000 | Muller et al. |
| 6,020,358 | A | 2/2000 | Muller et al. |
| 6,962,940 | B2 | 11/2005 | Muller et al. |
| 7,208,526 | B2 | 4/2007 | Boyd et al. |
| 7,659,302 | B2 | 2/2010 | Muller et al. |
| 7,893,101 | B2 | 2/2011 | Muller et al. |
| 8,124,646 | B2 | 2/2012 | Liu et al. |
| 8,242,310 | B2 | 8/2012 | Saindane et al. |
| 8,415,485 | B2 | 4/2013 | Frank et al. |
| 9,126,906 | B2 | 9/2015 | Connolly et al. |
| 9,187,417 | B2 | 11/2015 | Venkateswaralu et al. |

FOREIGN PATENT DOCUMENTS

| | | |
|---|---|---|
| DE | 2051871 | 11/1971 |
| WO | WO 2004/060313 | 7/2004 |
| WO | WO 2010/030345 | 3/2010 |
| WO | WO 2012/097116 | 7/2012 |

OTHER PUBLICATIONS

Lowe, 1998 "Tumour necrosis factor-antagonists and their therapeutic applications", Exp Opin Ther Patents 8(10): 1309-1322.
McCann et al., 2010, "Apremilast, a novel PDE4 inhibitor, inhibits spontaneous production of tumour necrosis factor-alpha from human rheumatoid synovial cells and ameliorates experimental arthritis", Arthritis Res Ther; 12(3):R107.
Schett et al., 2010, "Apremilast: a novel PDE4 inhibitor in the treatment of autoimmune and inflammatory diseases", Ther Adv Musculoskel Dis; 2(5):271-278.
Lai C. et al., "One-pot approach for the regioselective synthesis of beta-keto sulfones based on acid-catalyzed reaction of sulfonyl chlorides with arylacetylenes and water", Tetrahedron Letters, Jan. 17, 2005, pp. 513-515, vol. 46, No. 3, Elsevier, Amsterdam, NL.
F. Velasquez et al., 2006, "Steroselective synthesis of beta-substituted beta-amino sulfones and sulfonamides via addition of sulfonyl anions to chiral N-sulfinyl imines," Organic Letters, vol. 8, No. 6, 2006, pp. 789-792.
Hua Zhang et al., 2011, "Practical and stereoselective synthesis of beta-amino sulfones from alkylphenylsulfones and N-(tert-butylsulfinyl)aldimines," Organic and Biomolecular Chemistry, vol. 9, 2011, pp. 6502-6505.
Guangcheng Liu et al., 1999, "Synthesis of enantiomerically pure N-tert-butanesulfinyl 1m1nes (tert-butanesulfinimines) by the direct condensation of tert-butanesulfinamide with aldehydes and ketones," Journal of Organic Chemistry, vol. 64, No. 4, 1999, pp. 1278-1284.
Panteleimonov, A. G. et al., 1966, "Addition of nucleophilic agents to 1-aryl-2-trifluoro-methylsulfonylethylenes," Zhurnal Obshchei Khimii, 36(11), 1966, 1976-80, XP-002712273.
Balasubramanian M et al., 1955, "Synthesis of Beta-Amino-Sulphones and Alphabeta-Unsaturated Sulphones. Part II," Journal of the Chemical Society, Chemical Society, Letchworth; GB, 1955, pp. 3296-3298, XP-001069585.
Ward et al., 2010, "High-yield biocatalytic amination reactions in organic synthesis," Current Organic Chemistry, 14.17 (2010): 1914-1927.
Becker et al., 1963, "Preparation of β-Keto Sulfones by Condensation of Aromatic Esters with Dimethyl Sulfone1,2," *J Org. Chem.*, 1963, 28(7), 1896-8.

*Primary Examiner* — Clinton Brooks
(74) *Attorney, Agent, or Firm* — Jones Day

(57) ABSTRACT

Provided herein are new processes for the preparation of aminosulfone intermediates for the synthesis of 2-[1-(3-ethoxy-4-methoxyphenyl)-2-methylsulfonylethyl]-4-acetylaminoisoindoline-1,3-dione, which is useful for preventing or treating diseases or conditions related to an abnormally high level or activity of TNF-α. Further provided herein are processes for the commercial production of (S)-1-(3-ethoxy-4-methoxyphenyl)-2-methanesulfonylethylamine.

9 Claims, No Drawings

PROCESSES FOR THE PREPARATION OF (S)-1-(3-ETHOXY-4-METHOXYPHENYL)-2-METHANESULFONYLETHYLAMINE

This application is a divisional of U.S. application Ser. No. 14/882,564, filed Oct. 14, 2015, currently allowed, which is a divisional of U.S. application Ser. No. 13/771,164, filed Feb. 20, 2013, now U.S. Pat. No. 9,187,417, issued Nov. 17, 2015, which claims the benefit of priority to U.S. Provisional Application Ser. No. 61/601,226, filed Feb. 21, 2012, the entire contents of each of which are incorporated herein by reference in its entirety and for all purposes.

1. FIELD

Provided herein are new processes for the preparation of aminosulfone intermediates for the synthesis of 2-[1-(3-ethoxy-4-methoxyphenyl)-2-methylsulfonylethyl]-4-acetylaminoisoindoline-1,3-dione, which is useful for preventing or treating diseases or conditions related to an abnormally high level or activity of TNF-α. Further provided herein are processes for the commercial production of (S)-1-(3-ethoxy-4-methoxyphenyl)-2-methanesulfonylethylamine.

2. BACKGROUND

Inflammatory diseases such as arthritis, related arthritic conditions (e.g., osteoarthritis, rheumatoid arthritis, and psoriatic arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are prevalent and problematic ailments. Enhanced or unregulated TNF-α production plays a central role in the inflammatory response and the administration of their antagonists block chronic and acute responses in animal models of inflammatory disease. Many small-molecule inhibitors have demonstrated an ability to treat or prevent inflammatory diseases implicated by TNF-α (for a review, see Lowe, 1998 *Exp. Opin. Ther. Patents* 8:1309-1332). One such class of molecules is substituted phenethylsulfones as described in U.S. Pat. Nos. 6,020,358; 6,962,940; 7,208,526; and 7,659,302, and U.S. Patent Publication No. 2008/0234359, all of which are hereby incorporated by reference in their entirety. For example, the (+) enantiomer of 2-[1-(3-ethoxy-4-methoxyphenyl)-2-methylsulfonylethyl]-4-acetylaminoisoindoline-1,3-dione, also known as Apremilast, or a pharmaceutically acceptable prodrug, metabolite, polymorph, salt, solvate or clathrate thereof, is a novel oral pluripotent immunomodulator that specifically inhibits PDE4 and inhibits spontaneous production of TNF-α from human rheumatoid synovial cells and ameliorates experimental arthritis. (McCann et al., *Arthritis Res. Ther.* 2010, 12(3):R107). This compound is in an accelerated program for the treatment of psoriasis.

Without being limited by theory, the (+) enantiomer of 2-[1-(3-ethoxy-4-methoxyphenyl)-2-methylsulfonylethyl]-4-acetylaminoisoindoline-1,3-dione is believed to be (S)—N-(2-(1-(3-ethoxy-4-methoxyphenyl)-2-(methylsulfonyl)ethyl)-1,3-dioxoisoindolin-4-yl)acetamide, which has the following structure (Compound A):

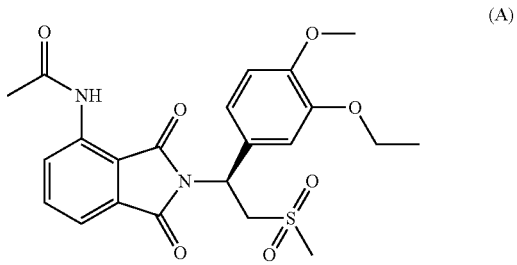 [SMILES: CCOc1cc([C@@H](CS(C)(=O)=O)N2C(=O)c3cccc(NC(C)=O)c3C2=O)ccc1OC]

Existing methods for synthesizing Compound A are described in U.S. Pat. No. 6,962,940, titled "(+)-2-[1-(3-Ethoxy-4-methoxyphenyl)-2-methylsulfonylethyl]-4-acetylaminoisoindoline-1,3-dione: Methods Of Using And Compositions Thereof," or U.S. Patent Publication No. 2010/0168475, each of which are incorporated herein by reference in their entirety. Generally, racemic 2-[1-(3-ethoxy-4-methoxyphenyl)-2-methylsulfonylethyl]-4-acetylaminoisoindoline-1,3-dione can be readily prepared using the methods described in U.S. Pat. No. 6,020,358, which is incorporated herein by reference in its entirety. The corresponding (+) enantiomer can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In a specific method, the (+) enantiomer of 2-[1-(3-ethoxy-4-methoxyphenyl)-2-methylsulfonylethyl]-4-acetylaminoisoindoline-1,3-dione is synthesized from 3-acetamidophthalic anhydride and a chiral amino acid salt of (S)-1-(3-ethoxy-4-methoxyphenyl)-2-methanesulfonylethylamine (Compound B).

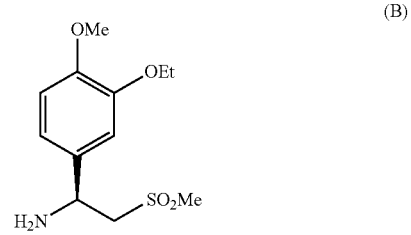 [SMILES: CCOc1cc([C@H](N)CS(C)(=O)=O)ccc1OC]

Chiral amino acid salts of (S)-1-(3-ethoxy-4-methoxyphenyl)-2-methanesulfonylethylamine include, but are not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. A specific chiral amino acid salt is (S)-1-(3-ethoxy-4-methoxyphenyl)-2-methanesulfonylethylamine N-acetyl-L-leucine salt, which is resolved from 1-(3-ethoxy-4-methoxyphenyl)-2-methanesulfonylethylamine and N-acetyl-L-leucine in methanol.

While these methods are enabling and useful for preparing Compound A, there are possibilities for alterations that may result in a more efficient, cost effective, commercially viable and safe synthesis.

Citation of any reference in Section 2 of this application is not to be construed as an admission that such reference is prior art to the present application.

3. SUMMARY

Provided herein are processes for the production of the key intermediate compound in the preparation of Apremilast, namely the aminosulfone (S)-1-(3-ethoxy-4-methoxyphenyl)-2-methanesulfonylethylamine (Compound B), that are cost effective and readily scaleable with commercial reagents, and do not involve any classical chiral separation. In one embodiment, provided herein are processes for preparing aminosulfones comprising the steps of: (a) coupling an optionally substituted benzonitrile with a dialkylsulfone; (b) hydrolyzing the coupled product to afford a beta-ketosulfone; (c) reacting the beta-ketosulfone with a chiral auxiliary to form a chiral enamine; (d) reducing the chiral enamine to afford an N-protected aminosulfone; and (e) optionally deprotecting the N-protected aminosulfone.

In another embodiment, provided herein are processes for preparing aminosulfones comprising the steps of: (a) condensing a chiral auxiliary with an aldehyde or ketone; (b) adding a nucleophile to the condensed product; and (c) deprotecting the addition product.

In yet other embodiments, provided herein are processes for preparing aminosulfones as set forth in Scheme 1, wherein R and $R^1$-$R^6$ are as described below.

In still other embodiments, provided herein are processes for preparing aminosulfones as set forth in Schemes 2 and 3, wherein $R^1$-$R^6$ are as described below.

In still another embodiment, the processes provided herein are useful for preparing aminosulfones or pharmaceutically acceptable salts, hydrates, solvates, or polymorphs thereof. In yet another embodiment, the processes provided herein are useful for preparing compounds useful for preventing or treating diseases or conditions related to an abnormally high level or activity of TNF-α. In yet another embodiment, the processes provided herein are useful for preparing compounds useful for treating or preventing inflammatory conditions.

4. DETAILED DESCRIPTION

4.1 Terminology

As used herein and unless otherwise indicated, the term "halo", "halogen", or the like means —F, —Cl, —Br, or —I.

As used herein and unless otherwise indicated, the term "lower molecular weight halo" means —F or —Cl.

As used herein and unless otherwise indicated, the term "higher molecular weight halo" means —Br or —I.

As used herein and unless otherwise indicated, the term "alkyl" means a saturated, monovalent, unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl. Longer alkyl groups include heptyl, octyl, nonyl and decyl groups. An alkyl group can be unsubstituted or substituted with one or more suitable substituents.

As used herein and unless otherwise indicated, the term "alkoxy" means an alkyl group that is linked to another group via an oxygen atom (i.e., —O-alkyl). An alkoxy group can be unsubstituted or substituted with one or more suitable substituents. Examples of alkoxy groups include, but are not limited to, ($C_1$-$C_6$)alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl and —O-hexyl.

As used herein and unless otherwise indicated, the term "lower alkyl" means alkyl having from 1 to 4 carbon atoms. Examples include, but are not limited to, methyl, ethyl, propyl, isopropyl, isobutyl, and tertiary butyl ($^t$Bu, or t-butyl).

As used herein and unless otherwise indicated, the term "lower alkoxy" means a lower alkyl group that is linked to another group via an oxygen atom (i.e., —O-lower alkyl). Examples include, but are not limited to, methoxy, ethoxy, propoxy, isopropoxy, isobutoxy, and tertiary butoxy ($^t$OBu, or t-butoxy).

As used herein and unless otherwise indicated, the term "alcohol" means any compound substituted with an —OH group.

Unless otherwise indicated, the compounds provided herein, including intermediates useful for the preparation of the compounds provided herein, which contain reactive functional groups (such as, without limitation, carboxy, hydroxy, and amino moeties) also include protected derivatives thereof. "Protected derivatives" are those compounds in which a reactive site or sites are blocked with one or more protecting groups (also known as blocking groups). Suitable protecting groups for carboxy moieties include benzyl, t-butyl, and the like. Suitable protecting groups for amino and amido groups include acetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in T. W. Green, "Protective Groups in Organic Synthesis", Third Ed., Wiley, New York, 1999, which is incorporated herein by reference in its entirety.

As used herein and unless otherwise indicated, the term "substituted" as used to describe a compound or chemical moiety means that at least one hydrogen atom of that compound or chemical moiety is replaced with a second chemical moiety. In one embodiment, the second chemical moiety may be any desired substituent that does not adversely affect the desired activity of the compound. Examples of substituents are those found in the exemplary compounds and embodiments disclosed herein, as well as halogen; $C_{1-8}$ alkyl; $C_{2-8}$ alkenyl; $C_{2-8}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (═O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; —NH(($C_1$-$C_8$)alkyl); —N(($C_1$-$C_8$)alkyl)$_2$; —NH(($C_6$)aryl); —N(($C_6$)aryl)$_2$; —CHO; —CO(($C_1$-$C_8$)alkyl); —CO(($C_6$)aryl); —CO$_2$(($C_1$-$C_8$)alkyl); and —CO$_2$(($C_6$)aryl); and such moieties may also be optionally substituted by a fused-ring structure or bridge, for example —OCH$_2$O—. These substituents may optionally be further substituted with a substituent selected from such groups.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereochemically pure" means a composition that comprises one stereoisomer of a compound and is substantially free of other stereoisomers of that compound. In certain embodiments as used herein, a composition with an enantiomeric excess ("ee") of about 99%, 95%, 90%, 85%, or 80% is stereochemically pure.

As used herein and unless otherwise indicated, the term "enantiomerically pure" means a stereomerically pure composition of a compound having one chiral center.

As used herein and unless otherwise indicated, the term "racemic" or "racemate" means about 50% of one enantiomer and about 50% of the corresponding enantiomer relative to all chiral centers in the molecule. The disclosure encompasses all enantiomerically pure, enantiomerically enriched, diastereomerically pure, diastereomerically enriched, and racemic mixtures of the compounds provided herein.

As used herein and unless otherwise indicated, the term "process(es) provided herein" refers to the methods disclosed herein which are useful for preparing a compound provided herein. Modifications to the methods disclosed herein (e.g., starting materials, reagents, protecting groups, solvents, temperatures, reaction times, purification) are also encompassed by the present embodiments.

As used herein and unless otherwise indicated, the term "adding" or the like means contacting one reactant, reagent, solvent, catalyst, or the like with another reactant, reagent, solvent, catalyst, or the like. Reactants, reagents, solvents, catalysts, or the like can be added individually, simultaneously, or separately and can be added in any order. They can be added in the presence or absence of heat and can optionally be added under an inert atmosphere.

As used herein and unless otherwise indicated, the term "coupling" or the like means covalently linking two or more reactants via chemical reaction(s). The linking can be facilitated by acid(s), base(s), activating agent(s), catalyst(s), and so on. The linking can occur in the presence or absence of heat, light, sound (sonication), microwave radiation, and so on and can optionally occur under an inert atmosphere.

As used herein and unless otherwise indicated, a reaction that is "substantially complete" or is driven to "substantial completion" means that the reaction contains more than about 80% by percent yield, more preferably more than about 90% by percent yield, even more preferably more than about 95% by percent yield, and most preferably more than about 97% by percent yield of the desired product.

As used herein and unless otherwise indicated, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. For example, specific pharmaceutically acceptable salts are hydrochloride, maleic acid, and tartaric acid salts.

As used herein and unless otherwise indicated, the term "hydrate" means a compound provided herein or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate, and the like).

As used herein and unless otherwise indicated, the term "polymorph" means solid crystalline forms of a compound provided herein or complex thereof. Different polymorphs of the same compound may exhibit different physical, chemical and/or spectroscopic properties.

As used herein and unless otherwise indicated, the term "tautomer" refers to isomeric forms of a compound that can be in equilibrium with each other. The concentrations of the isomeric forms will depend on the environment the compound is found in and may be different depending upon, for example, whether the compound is a solid or is in an organic or aqueous solution. For example, enamines and imines may exhibit the following isomeric forms, which are referred to as tautomers of each other:

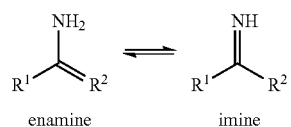

enamine    imine

As used herein and unless otherwise indicated, the phrase "diseases or conditions related to an abnormally high level or activity of TNF-α" means diseases or conditions that would not arise, endure, or cause symptoms if the level or activity of TNF-α were lower, or diseases or conditions that can be prevented or treated by a lowering of TNF-α level or activity.

As used herein and unless otherwise indicated, the term "treat", "treatment", "treating", or the like refers to the reduction or amelioration of the progression, severity and/or duration of a disease or condition, or the amelioration of one or more symptoms (preferably, one or more discernible symptoms) of a disease or condition resulting from the administration of one or more therapies (e.g., one or more therapeutic agents such as a compound provided herein).

As used herein and unless otherwise indicated, the term "prevent", "prevention", "preventing" or the like refers to the reduction in the risk of acquiring or developing a given disease or condition, or the reduction or inhibition of the recurrence, onset, or development of one or more symptoms of a given disease or condition.

Acronyms or symbols for groups or reagents have the following definition: ProtG=protecting group; Cbz=benzyloxycarbonyl; Boc=t-butyloxycarbonyl; Fmoc=9-fluorenylmethoxycarbonyl; p-TsOH=para-toluenesulfonic acid; TFA=trifluoroacetic acid; TMSCl=trimethylsilyl chloride; DMAP=N,N-dimethylaminopyridine; DBU=1,8-diazabicyclo[5.4.0]undec-7-ene; CDI=1,1'-carbonyldiimidazole; NBS=N-bromosuccinimide; VAZO®=1,1'-azobis-(cyclohexanecarbonitrile); DMF=N,N-dimethylformamide; THF=tetrahydrofuran; DCM=dichloromethane; MTBE=methyl tert-butyl ether.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

The embodiments provided herein can be understood more fully by reference to the following detailed description and illustrative examples, which are intended to exemplify non-limiting embodiments of the invention.

4.2 Processes

Provided herein are cost-effective and efficient processes for the commercial production of chiral aminosulfones, which may be intermediates for the synthesis of 2-[1-(3-ethoxy-4-methoxyphenyl)-2-methylsulfonylethyl]-4-acetylaminoisoindoline-1,3-dione (Apremilast), which is useful for preventing or treating diseases or conditions related to an abnormally high level or activity of TNF-α. In particular, provided herein are processes for the commercial production of (S)-1-(3-ethoxy-4-methoxyphenyl)-2-methanesulfonylethylamine (Compound B).

In some embodiments, the processes provided herein utilize a chiral auxiliary for inducing chirality and eliminating the need for classic resolution. In other embodiments, the processes provided herein utilize enzymatic transamination. In other embodiments, the processes provided herein utilize asymmetric epoxidation and ring-opening.

In one embodiment, provided herein are processes for preparing a compound of Formula I:

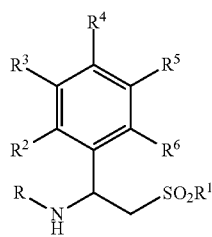

(I)

or a pharmaceutically acceptable salt, hydrate, solvate, or polymorph thereof, wherein:
R is —CH(C$_1$-C$_6$alkyl)Ar or hydrogen;
R$^1$ is C$_1$-C$_6$alkyl;

each of R$^2$, R$^3$, R$^4$, R$^5$, and R$^6$ is at each occurrence independently hydrogen, halo, C$_1$-C$_6$alkyl, C$_1$-C$_6$alkoxy, —CF$_3$, —CN or —NO$_2$; and
Ar is aryl,
which comprises the alternative sequences of steps of: (a) coupling an optionally substituted benzonitrile with a dialkylsulfone; (b) hydrolyzing the coupled product to afford a beta-ketosulfone; (c) reacting the beta-ketosulfone with a chiral auxiliary to form a chiral enamine; (d) reducing the chiral enamine to afford an N-protected aminosulfone; and (e) optionally deprotecting the N-protected aminosulfone.

In one embodiment, provided herein are processes described above for preparing a compound of Formula I wherein R is —CH(CH$_3$)phenyl.

In one embodiment, provided herein are processes described above for preparing a compound of Formula I wherein R is hydrogen.

In one embodiment, provided herein are processes described above for preparing a compound of Formula I wherein R$^1$ is —CH$_3$.

In one embodiment, provided herein are processes described above for preparing a compound of Formula I wherein R$^2$, R$^3$ and R$^6$ are each H and R$^4$ and R$^5$ are each C$_1$-C$_6$alkoxy.

In one embodiment, provided herein are processes described above for preparing a compound of Formula I wherein R is —CH(C$_1$-C$_6$alkyl)aryl, R$^2$, R$^3$ and R$^6$ are each H, R$^1$ is C$_1$-C$_6$alkyl, R$^4$ is C$_1$-C$_6$alkoxy, and R$^5$ is C$_1$-C$_6$alkoxy.

In one embodiment, provided herein are processes described above for preparing a compound of Formula I wherein R is —CH(CH$_3$)phenyl, R$^2$, R$^3$ and R$^6$ are each H, R$^1$ is —CH$_3$, R$^4$ is —OCH$_3$, and R$^5$ is —OCH$_2$CH$_3$.

In one embodiment, provided herein are processes described above for preparing a compound of Formula I wherein R, R$^2$, R$^3$ and R$^6$ are each H, R$^1$ is C$_1$-C$_6$alkyl, R$^4$ is C$_1$-C$_6$alkoxy, and R$^5$ is C$_1$-C$_6$alkoxy.

In one embodiment, provided herein are processes described above for preparing a compound of Formula I wherein R, R$^2$, R$^3$ and R$^6$ are each H, R$^1$ is —CH$_3$, R$^4$ is —OCH$_3$, and R$^5$ is —OCH$_2$CH$_3$.

In some embodiments, the coupling step in the process described above occurs under basic condition. In some embodiments, the hydrolyzing step in the process described above occurs under acidic condition. In some embodiments, reacting with a chiral auxiliary step described in the process above occurs in the presence of an acid. In some embodiments, the chiral enamine is reduced in achiral conditions to afford an N-protected aminosulfone.

In one embodiment, the benzonitrile is 3-ethoxy-4-methoxybenzonitrile. In one embodiment, the dialkylsulfone is dimethylsulfone. In one embodiment, the chiral auxiliary is (S)-α-methylbenzylamine, which is also known as (S)-phenylethylamine. In one embodiment, the chiral auxiliary is (R)-tert-butylsulfinamide. In one embodiment, the acid used when reacting a chiral auxiliary is a Lewis acid. In one embodiment, the acid used when reacting with a chiral auxiliary is the Lewis acid titanium tetraethoxide (Ti(OEt)$_4$). In one embodiment, the acid used when reacting with a chiral auxiliary is the Bronsted acid para-toluenesulfonic acid (p-TsOH). In one embodiment, the deprotecting the N-protected aminosulfone is via debenzylation. In one embodiment, the debenzylation is via catalytic hydrogenation. In one embodiment, the reducing agent is sodium borohydride (NaBH$_4$).

In some embodiments, provided herein are processes for preparing aminosulfones comprising the diastereoselective reduction of an enamine derived from a chiral auxiliary as depicted in Scheme 1 below.

SCHEME 1

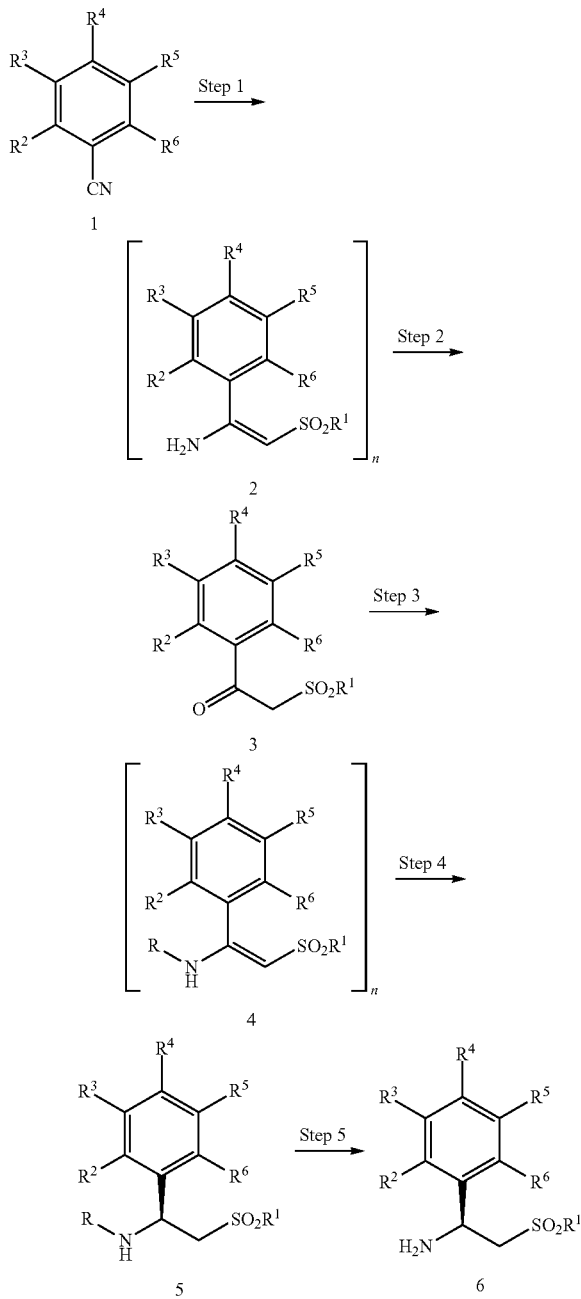

In these embodiments, each of R, $R^1$, $R^2$, $R^3$, $R^4$, $R^5$, and $R^6$ is as defined above. In one embodiment of Scheme 1, Step 1 is characterized as coupling, Step 2 is enamine hydrolysis, Step 3 is enamine formation with the chiral auxiliary, Step 4 is diastereoselective enamine reduction, and Step 5 is optional deprotection of the N-protected aminosulfone.

In one embodiment of Scheme 1, in Step 1, dimethylsulfone ($R^1$=—$CH_3$) is deprotonated with butyllithium, and to the resulting anion is added 3-ethoxy-4-methoxybenzonitrile 1 (wherein $R^2$=$R^3$=$R^6$=H; $R^4$=—$OCH_3$, $R^5$=—$OCH_2CH_3$). The resulting enamine 2 (wherein $R^1$=—$CH_3$) is then hydrolyzed in Step 2 with aqueous HCl to provide the β-ketosulfone 3. This intermediate is then reacted in Step 3 with the chiral auxiliary (S)-α-methylbenzylamine in the presence of 2.0 equivalents titanium tetraethoxide or a catalytic amount (0.2. equivalents) of para-toluenesulfonic acid to form the chiral enamine 4 (wherein R=(S)-α-methylbenzyl), which is not isolated, but instead is reduced in situ in Step 4 by the addition of sodium borohydride and acetic acid, to provide a benzyl-protected amino sulfone 5. In one embodiment, the compound 5 may optionally be purified by conversion to a salt (e.g., a hydrochloride salt), then isolated (e.g., as the isopropanol solvate HCl salt). In the final Step 5, debenzylation via catalytic hydrogenation over 10% Pd—C or 5% Pd—C catalyst in methanol selectively removes the α-methylbenzyl group "R" and delivers the aminosulfone 6, which is Compound B (wherein R=$R^2$=$R^3$=$R^6$=H; $R^1$=—$CH_3$, $R^4$=—$OCH_3$, $R^5$=—$OCH_2CH_3$).

In one embodiment, provided herein are processes described above for preparing a compound of Formula I wherein R is —CH($CH_3$)phenyl.

In one embodiment, provided herein are processes described above for preparing a compound of Formula I wherein R is hydrogen.

In one embodiment of Scheme 1, provided herein are processes described above for preparing a compound of Formula I wherein $R^1$ is —$CH_3$.

In one embodiment of Scheme 1, provided herein are processes described above for preparing a compound of Formula I wherein $R^2$, $R^3$ and $R^6$ are each H and $R^4$ and $R^5$ are each $C_1$-$C_6$alkoxy.

In one embodiment of Scheme 1, provided herein are processes described above for preparing a compound of Formula I wherein R is —CH($C_1$-$C_6$alkyl)aryl, $R^2$, $R^3$ and $R^6$ are each H, le is $C_1$-$C_6$alkyl, $R^4$ is $C_1$-$C_6$alkoxy, and $R^5$ is $C_1$-$C_6$alkoxy.

In one embodiment of Scheme 1, provided herein are processes described above for preparing a compound of Formula I wherein R is —CH($CH_3$)phenyl, $R^2$, $R^3$ and $R^6$ are each H, $R^1$ is —$CH_3$, $R^4$ is —$OCH_3$, and $R^5$ is —$OCH_2CH_3$.

In one embodiment of Scheme 1, provided herein are processes described above for preparing a compound of Formula I wherein R, $R^2$, $R^3$ and $R^6$ are each H, $R^1$ is $C_1$-$C_6$alkyl, $R^4$ is $C_1$-$C_6$alkoxy, and $R^5$ is $C_1$-$C_6$alkoxy.

In one embodiment of Scheme 1, provided herein are processes described above for preparing a compound of Formula I wherein R, $R^2$, $R^3$ and $R^6$ are each H, $R^1$ is —$CH_3$, $R^4$ is —$OCH_3$, and $R^5$ is —$OCH_2CH_3$.

In another embodiment, provided herein are processes for preparing a compound of Formula II:

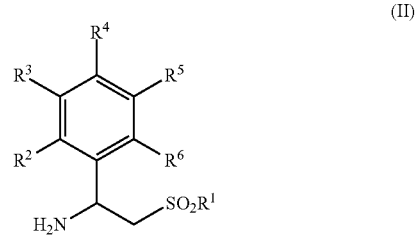

(II)

or a pharmaceutically acceptable salt, hydrate, solvate, or polymorph thereof, wherein:

$R^1$ is $C_1$-$C_6$alkyl; and each of $R^2$, $R^3$, $R^4$, $R^5$, and $R^6$ is at each occurrence independently hydrogen, halo, $C_1$-$C_6$alkyl, $C_1$-$C_6$alkoxy, —$CF_3$, —CN or —$NO_2$;

which comprises the alternative sequences of steps of: (a) condensing a chiral auxiliary with an aldehyde or ketone; (b) adding a nucleophile to the condensed product; and (c) deprotecting the addition product.

In one embodiment, provided herein are processes described above for preparing a compound of Formula II wherein $R^1$ is —$CH_3$.

In one embodiment, provided herein are processes described above for preparing a compound of Formula II wherein $R^2$, $R^3$ and $R^6$ are each H and $R^4$ and $R^5$ are each $C_1$-$C_6$alkoxy.

In one embodiment, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment, provided herein are processes described above for preparing a compound of Formula II wherein $R^2$, $R^3$ and $R^6$ are each H; $R^1$ is —$CH_3$, $R^4$=—$OCH_3$, and $R^5$ is —$OCH_2CH_3$.

In some embodiments, the addition step in the process described above occurs under basic condition. In some embodiments, deprotecting the addition product occurs under acidic condition.

In one embodiment of this process, the aldehyde is 3-ethoxy-4-methoxybenzaldehyde. In one embodiment of this process, the chiral auxiliary is (R)-(+)-tertiarybutylsulfinamide or (R)-tert-butylsulfinamide (so-called Ellman's auxiliary). See Liu et al., *JACS*, (1997) 119:9913. In another embodiment of this process, the chiral auxiliary is (S)-α-methylbenzylamine. In one embodiment of this process, the nucleophile is the lithium anion of dimethylsulfone, which may optionally be prepared by deprotonation with butyl-lithium.

Condensation of commercially available tert-butanesulfinamide with aldehydes and ketones proceeds under mild conditions and provides tert-butanesulfinyl imines in high yields. The tert-butanesulfinyl group activates these imines for the addition of many different classes of nucleophiles. Subsequent removal of the tert-butanesulfinyl group under mild conditions cleanly provides the amine products. There tert-butanesulfinyl imines have been used as intermediates in the asymmetric synthesis of many versatile building blocks (Ellman et al., *Acc. Chem. Res.*, (2002) 35:984) including beta-amino acids and esters (see, e.g., Jacobsen and Skrydstrup, *J. Org. Chem.*, (2003) 68:7122; Tang and Ellman, *J. Org. Chem.*, (2002) 67:7819; Tang and Ellman, *J. Org. Chem.*, (1999) 64:12).

In some embodiments, provided herein are processes for preparing aminosulfones comprising the diastereoselective addition to an imine derived from a chiral auxiliary as depicted in Scheme 2 below.

SCHEME 2

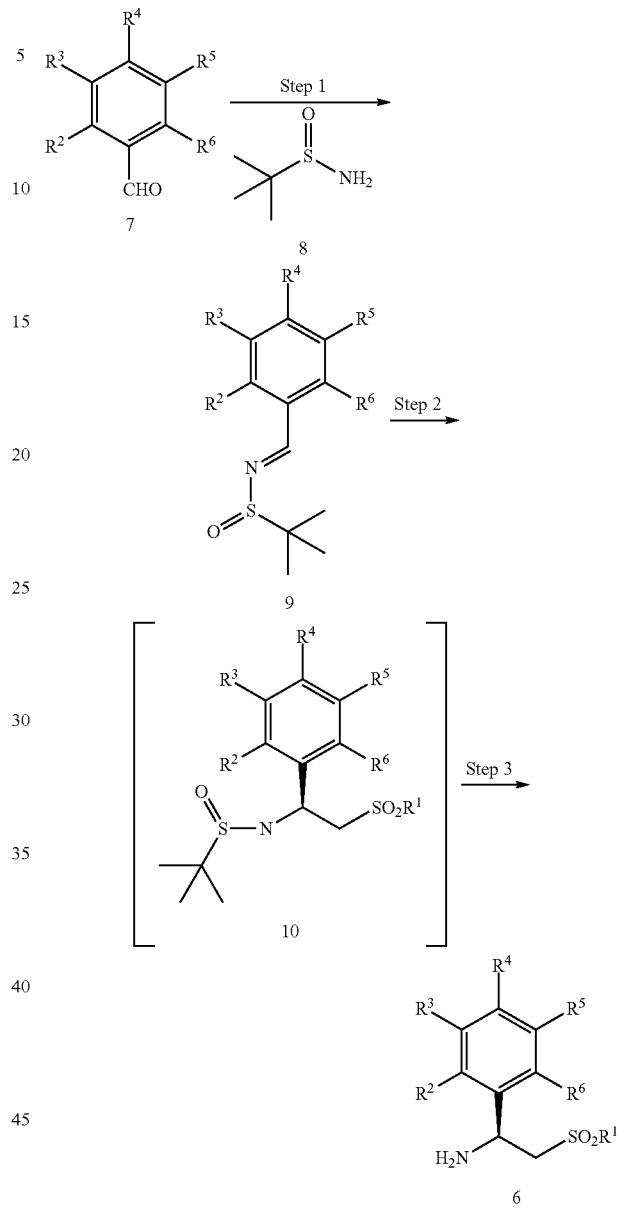

In these embodiments, each of $R^1$, $R^2$, $R^3$, $R^4$, $R^5$, and $R^6$ is at each occurrence as defined above. In one embodiment of Scheme 2, Step 1 is characterized as imine formation, Step 2 is diastereoselective addition, Step 3 is deprotection of the N-protected aminosulfone.

In one embodiment of Scheme 2, in Step 1, 3-ethoxy-4-methoxybenzaldehyde 7 (wherein $R^2$=$R^3$=$R^6$=H; $R^4$=—$OCH_3$, $R^5$=—$OCH_2CH_3$) is condensed with (R)-(+)-tertiarybutylsulfinamide (so-called Ellman's auxiliary) 8 to afford imine 9. In Step 2, dimethylsulfone ($R^1$=—$CH_3$) is deprotonated with butyllithium, then added to imine 9. In the final Step 3, the resulting addition product intermediate 10 is then deprotected under mild conditions (e.g., HCl in methanol) to afford the aminosulfone 6, which is Compound B (wherein $R^2$=$R^3$=$R^6$=H; $R^1$=—$CH_3$, $R^4$=—$OCH_3$, $R^5$=—$OCH_2CH_3$).

In one embodiment of Scheme 2, provided herein are processes described above for preparing a compound of Formula II wherein $R^1$ is —$CH_3$.

In one embodiment of Scheme 2, provided herein are processes described above for preparing a compound of Formula II wherein $R^2$, $R^3$ and $R^6$ are each H and $R^4$ and $R^5$ are each $C_1$-$C_6$alkoxy.

In one embodiment of Scheme 2, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment of Scheme 2, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In some embodiments, provided herein are processes for preparing aminosulfones comprising the diastereoselective addition to an imine derived from a chiral auxiliary as depicted in Scheme 3 below.

SCHEME 3

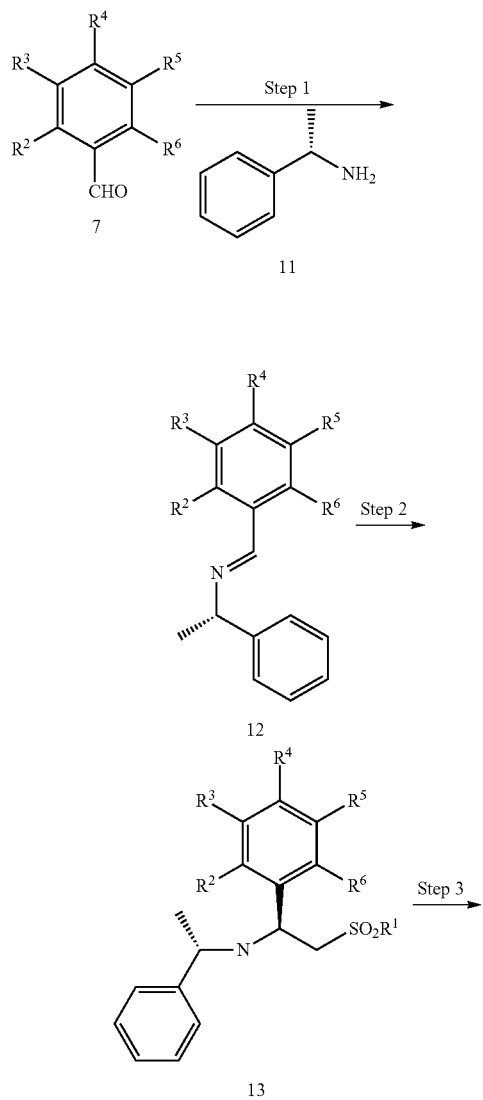

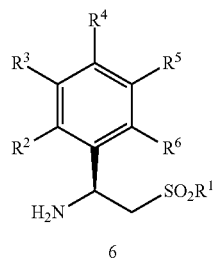

6

In these embodiments, each of $R^1$, $R^2$, $R^3$, $R^4$, $R^5$, and $R^6$ is at each occurrence as defined above. In one embodiment of Scheme 3, Step 1 is characterized as imine formation, Step 2 is diastereoselective addition, Step 3 is deprotection of the N-protected aminosulfone.

In one embodiment of Scheme 3, in Step 1, 3-ethoxy-4-methoxybenzaldehyde 7 (wherein $R^2$=$R^3$=$R^6$=H; $R^4$=—$OCH_3$, $R^5$=—$OCH_2CH_3$) is condensed with (S)-α-methylbenzylamine 11 to afford imine 12. In Step 2, dimethylsulfone ($R^1$=—$CH_3$) is deprotonated with butyllithium, then added to imine 12 (for an example of diastereoselective addition to imine see e.g., U.S. Pat. No. 5,932,749, wherein allyl Grignard was added to the (S)-α-methylbenzylamine of 3,4-methylenedioxybenzaldehyde in 82% yield and 99% d.e.). In the final Step 3, the resulting addition product intermediate 13 (note that this is the same product that can be derived as Compound 5 in certain embodiments of Scheme 1 above) is then deprotected (e.g., catalytic hydrogenation) to afford the aminosulfone 6, which is Compound B (wherein $R^2$=$R^3$=$R^6$=H; $R^1$=—$CH_3$, $R^4$=—$OCH_3$, $R^5$=—$OCH_2CH_3$).

In one embodiment of Scheme 3, provided herein are processes described above for preparing a compound of Formula II wherein $R^1$ is —$CH_3$.

In one embodiment of Scheme 3, provided herein are processes described above for preparing a compound of Formula II wherein $R^2$, $R^3$ and $R^6$ are each H and $R^4$ and $R^5$ are each $C_1$-$C_6$alkoxy.

In one embodiment of Scheme 3, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment of Scheme 3, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In another embodiment, provided herein are processes for preparing aminosulfones comprising the diastereoselective addition to of a chiral auxiliary to an achiral sulfone as depicted in Scheme 4 below.

SCHEME 4

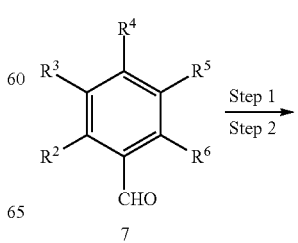

7

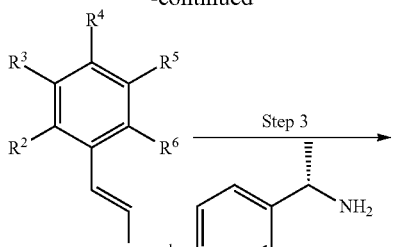

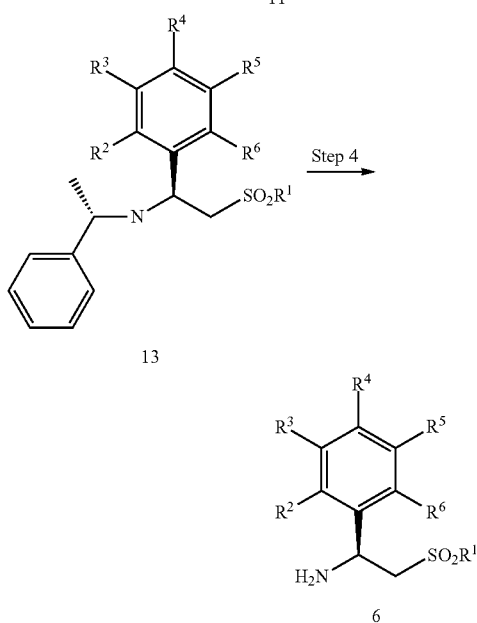

In these embodiments, each of $R^1$, $R^2$, $R^3$, $R^4$, $R^5$, and $R^6$ is at each occurrence as defined above. In one embodiment of Scheme 4, Step 1 is characterized as nucleophilic addition, Step 2 is dehydration, Step 3 is diastereoselective addition, and Step 4 is deprotection of the N-protected aminosulfone.

In one embodiment of Scheme 4, in Steps 1 and 2, 3-ethoxy-4-methoxybenzaldehyde 7 (wherein $R^2=R^3=R^6=H$; $R^4=$—$OCH_3$, $R^5=$—$OCH_2CH_3$) is condensed with a dialkylsulfone (e.g., dimethylsulfone deprotonated with butyllithium, wherein $R^1=$—$CH_3$), to afford α,β-unsaturated styryl sulfone 14. In Step 3, chiral auxiliary (S)-α-methylbenzylamine 11, which may be deprotonated (e.g., with butyllithium base) or in neutral form, is added to addition product 14 to afford intermediate product 13 (note that this is the same product that can be derived as Compound 5 in certain embodiments of Scheme 1 above). In the final Step 4, product 13 is then deprotected (e.g., catalytic hydrogenation) to afford the aminosulfone 6, which is Compound B (wherein $R^2=R^3=R^6=H$; $R^1=$—$CH_3$, $R^4=$—$OCH_3$, $R^5=$—$OCH_2CH_3$).

In one embodiment of Scheme 4, provided herein are processes described above for preparing a compound of Formula II wherein $R^1$ is —$CH_3$.

In one embodiment of Scheme 4, provided herein are processes described above for preparing a compound of Formula II wherein $R^2$, $R^3$ and $R^6$ are each H and $R^4$ and $R^5$ are each $C_1$-$C_6$alkoxy.

In one embodiment of Scheme 4, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment of Scheme 4, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In other embodiments, provided herein are processes for preparing aminosulfones comprising enzymatic transamination as depicted in Scheme 5 below.

SCHEME 5

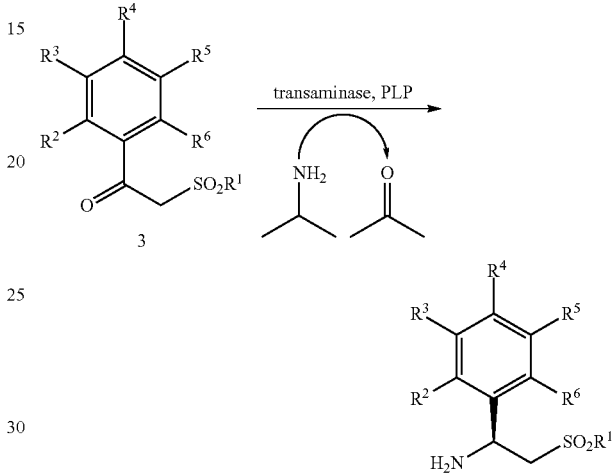

In these embodiments, each of $R^1$, $R^2$, $R^3$, $R^4$, $R^5$, and $R^6$ is at each occurrence as defined above. Biocatalytic production of amines uses enzymes of the transaminase class, which transfer the amino group from a donor organic compound such as isopropyl amine to a ketone or aldehyde acceptor (Curr. Org. Chem, (2010), 14:1914-1927; for an example of using enzymatic transamination in an API-forming step see Angew. Chem. Int. Ed., (2011), 50:1974-1976). In certain embodiments provided herein, the substrate would be the β-ketosulfone 3, which is also an intermediate in schemes described herein.

In one embodiment of Scheme 5, provided herein are processes described above for preparing a compound of Formula II wherein $R^1$ is —$CH_3$.

In one embodiment of Scheme 5, provided herein are processes described above for preparing a compound of Formula II wherein $R^2$, $R^3$ and $R^6$ are each H and $R^4$ and $R^5$ are each $C_1$-$C_6$alkoxy.

In one embodiment of Scheme 5, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment of Scheme 5, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In other embodiments, provided herein are processes for preparing aminosulfones comprising diastereoselective borohydride reduction of a chiral auxiliary adduct as depicted in Scheme 6 below.

SCHEME 6

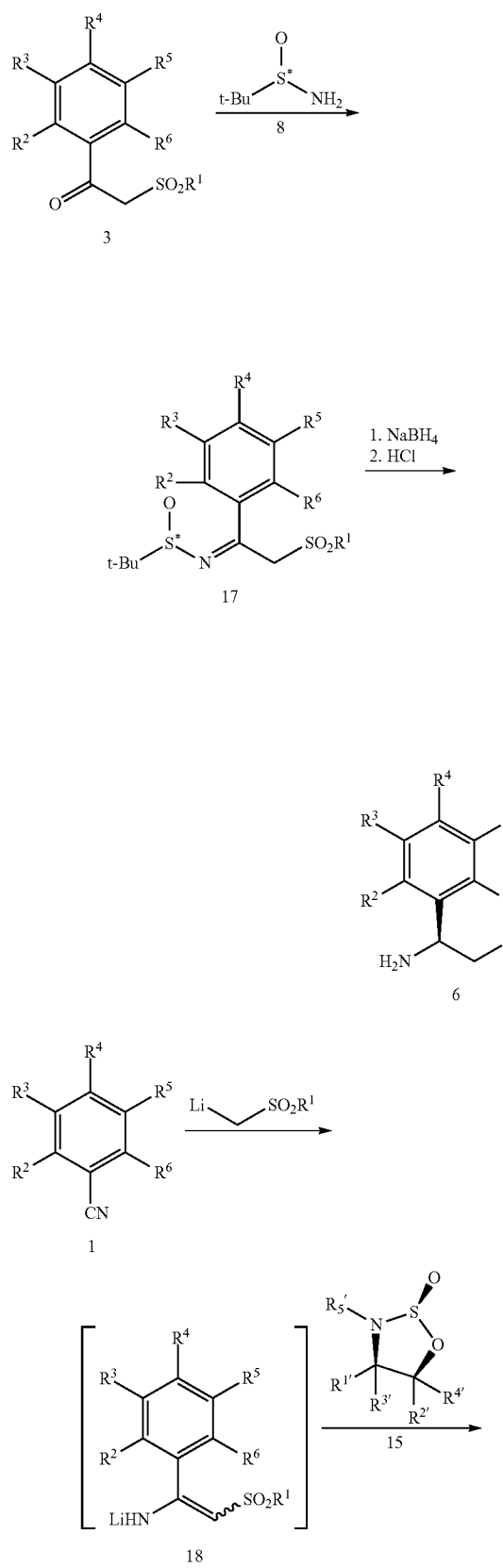

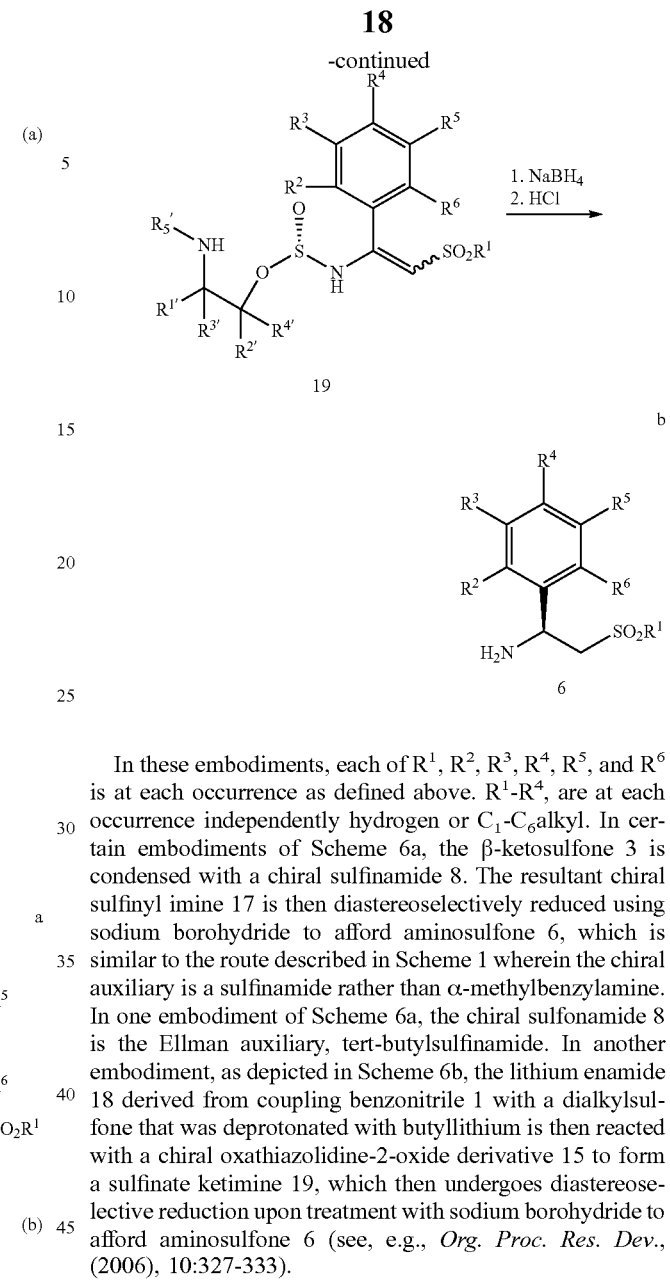

In these embodiments, each of $R^1$, $R^2$, $R^3$, $R^4$, $R^5$, and $R^6$ is at each occurrence as defined above. $R^1$-$R^4$, are at each occurrence independently hydrogen or $C_1$-$C_6$alkyl. In certain embodiments of Scheme 6a, the β-ketosulfone 3 is condensed with a chiral sulfinamide 8. The resultant chiral sulfinyl imine 17 is then diastereoselectively reduced using sodium borohydride to afford aminosulfone 6, which is similar to the route described in Scheme 1 wherein the chiral auxiliary is a sulfinamide rather than α-methylbenzylamine. In one embodiment of Scheme 6a, the chiral sulfonamide 8 is the Ellman auxiliary, tert-butylsulfinamide. In another embodiment, as depicted in Scheme 6b, the lithium enamide 18 derived from coupling benzonitrile 1 with a dialkylsulfone that was deprotonated with butyllithium is then reacted with a chiral oxathiazolidine-2-oxide derivative 15 to form a sulfinate ketimine 19, which then undergoes diastereoselective reduction upon treatment with sodium borohydride to afford aminosulfone 6 (see, e.g., Org. Proc. Res. Dev., (2006), 10:327-333).

In one embodiment of Scheme 6, provided herein are processes described above for preparing a compound of Formula II wherein $R^1$ is —$CH_3$.

In one embodiment of Scheme 6, provided herein are processes described above for preparing a compound of Formula II wherein $R^2$, $R^3$ and $R^6$ are each H and $R^4$ and $R^5$ are each $C_1$-$C_6$alkoxy.

In certain embodiments of Scheme 6, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In certain embodiments of Scheme 6, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In still other embodiments, provided herein are processes for preparing aminosulfones comprising stereoselective addition of an aryl anion to aldimine with chiral auxiliary as depicted in Scheme 7 below.

SCHEME 7

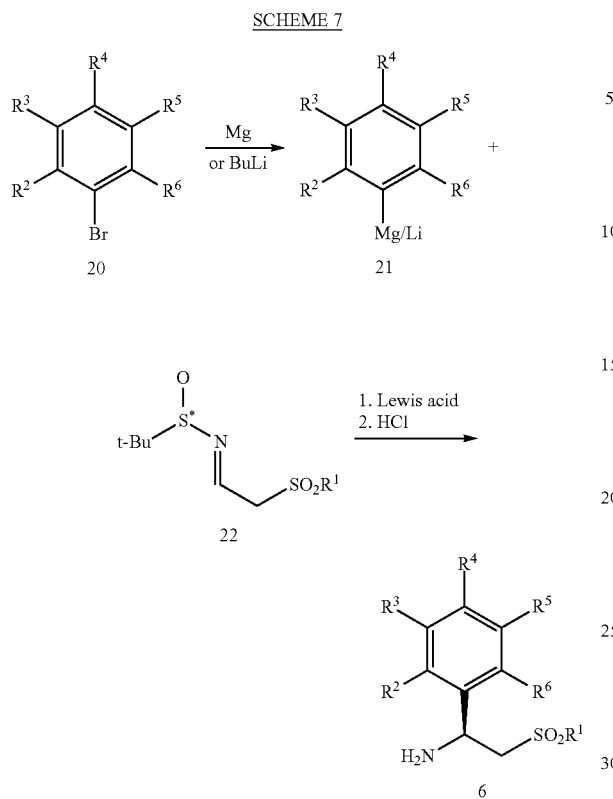

SCHEME 8

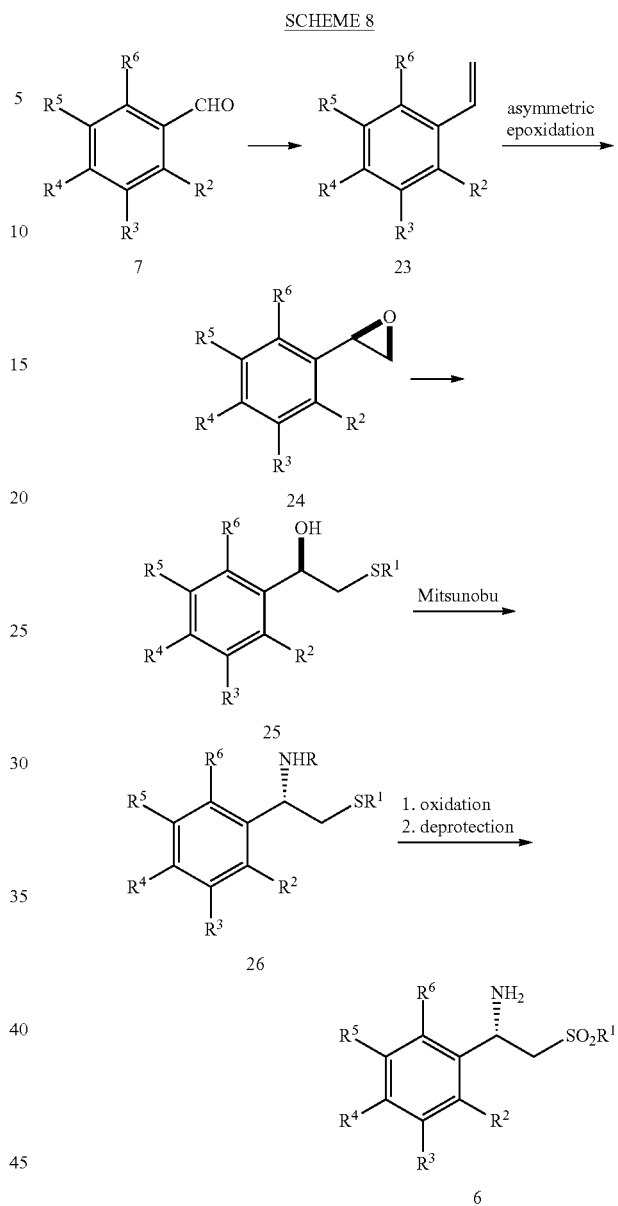

In these embodiments, each of $R^1$, $R^2$, $R^3$, $R^4$, $R^5$, and $R^6$ is at each occurrence as defined above. In certain embodiments of Scheme 7, a metalated arene 21 made from bromobenzene 20 is reacted with a chiral sulfinylimine derivative 22 of 2-(methylsulfonyl)acetaldehyde (e.g., chiral tert-butyl sulfinylimine). In some embodiments of Scheme 7, it is necessary to activate the sulfinyl imine, for example with a Lewis acid such as boron trifluoride. Diastereoselective additions affords the sulfonamide, and subsequent hydrolysis then provides the chiral aminosulfone 6. Similar transformations have been reported in the literature (*JACS*, (1997), 119:9913-9914; *Tet. Lett.*, (2001), 42:2051-2054).

In one embodiment of Scheme 7, provided herein are processes described above for preparing a compound of Formula II wherein $R^1$ is —$CH_3$.

In one embodiment of Scheme 7, provided herein are processes described above for preparing a compound of Formula II wherein $R^2$, $R^3$ and $R^6$ are each H and $R^4$ and $R^5$ are each $C_1$-$C_6$alkoxy.

In one embodiment of Scheme 7, provided herein are processes described above for preparing a compound of Formula II wherein $R^2$, $R^3$ and $R^6$ are each H; $R^1$ is $C_1$-$C_6$alkyl, $R^4$ is $C_1$-$C_6$alkoxy, and $R^5$ is $C_1$-$C_6$alkoxy.

In one embodiment of Scheme 7, provided herein are processes described above for preparing a compound of Formula II wherein $R^2$, $R^3$ and $R^6$ are each H; $R^1$ is —$CH_3$, $R^4$ is —$OCH_3$, and $R^5$ is —$OCH_2CH_3$.

In another embodiment, provided herein are processes for preparing aminosulfones comprising asymmetric epoxidation and ring-opening with a sulfur nucleophile as depicted in Scheme 8 below.

In these embodiments, each of $R^1$, $R^2$, $R^3$, $R^4$, $R^5$, and $R^6$ is at each occurrence as defined above. In certain embodiments of Scheme 8, conversion of benzaldehyde 7 to the corresponding styrene 23 can be accomplished by various methylenation reactions, for example the Wittig reaction. Subsequent asymmetric epoxidation then provides a chiral epoxide 24; various methods for asymmetric epoxidation of styrenes to provide enantiomerically enriched styrene oxides are known in the literature (*Tet.*, (2010), 66:6309-6320; *J. Inorg. Organomet. Polym*, (2010), 20:675-683). This epoxide can be opened with a sulfur nucleophile such as thiomethoxide ($R^1$=—$CH_3$) to give a 2-(alkylthio)ethanol derivative 25. Routine functional group interconversion, such as with the Mitsunobu reaction, is then be used to convert the alcohol to an amine 26 (free or protected), with retention or inversion of configuration as needed. Oxidation of the sulfide to a sulfone, followed by optional nitrogen deprotection provides the chiral aminosulfone 6.

In one embodiment of Scheme 8, provided herein are processes described above for preparing a compound of Formula II wherein $R^1$ is —CH$_3$.

In one embodiment of Scheme 8, provided herein are processes described above for preparing a compound of Formula II wherein $R^2$, $R^3$ and $R^6$ are each H and $R^4$ and $R^5$ are each C$_1$-C$_6$alkoxy.

In certain embodiments of Scheme 8, provided herein are processes described above for preparing a compound of Formula II wherein $R^2$, $R^3$ and $R^6$ are each H; $R^1$ is C$_1$-C$_6$alkyl, $R^4$ is C$_1$-C$_6$alkoxy, and $R^5$ is C$_1$-C$_6$alkoxy.

In certain embodiments of Scheme 8, provided herein are processes described above for preparing a compound of Formula II wherein $R^2$, $R^3$ and $R^6$ are each H; $R^1$ is —CH$_3$, $R^4$ is —OCH$_3$, and $R^5$ is —OCH$_2$CH$_3$.

4.3 Compounds

In certain embodiments, provided herein are compounds of Formula (III):

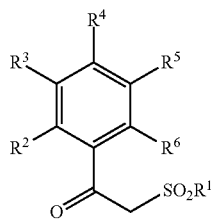

(III)

and pharmaceutically acceptable salts, hydrates, solvates, and polymorphs thereof, wherein:

$R^1$ is C$_1$-C$_6$alkyl; and each of $R^2$, $R^3$, $R^4$, $R^5$, and $R^6$ is at each occurrence independently hydrogen, halo, alkyl, alkoxy, —CF$_3$, —CN or —NO$_2$.

In one embodiment, provided herein are compounds of Formula (III), wherein $R^1$ is —CH$_3$.

In one embodiment, provided herein are compounds of Formula (III), wherein $R^2$, $R^3$ and $R^6$ are each H and $R^4$ and $R^5$ are each C$_1$-C$_6$alkoxy.

In one embodiment, provided herein are compounds of Formula (III), wherein $R^1$ is alkyl; $R^2$ is H; $R^3$ is H; $R^4$ is C$_1$-C$_6$alkoxy; $R^5$ is C$_1$-C$_6$alkoxy; and $R^6$ is H.

In one embodiment, provided herein are compounds of Formula (III), wherein $R^1$ is —CH$_3$; $R^2$ is H; $R^3$ is H; $R^4$ is —OCH$_3$; $R^5$ is —OCH$_2$CH$_3$; and $R^6$ is H.

In one embodiment, the compound of Formula (III) is:

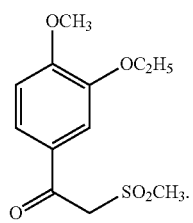

In certain embodiments, provided herein are compounds of Formula (IV):

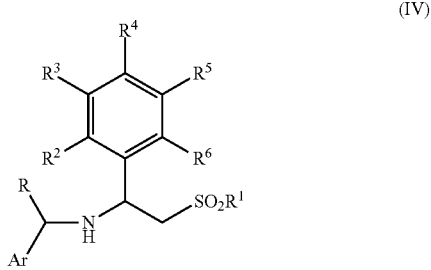

(IV)

and pharmaceutically acceptable salts, hydrates, solvates, and polymorphs thereof, wherein:

R is C$_1$-C$_6$alkyl;

$R^1$ is C$_1$-C$_6$alkyl;

each of $R^2$, $R^3$, $R^4$, $R^5$, and $R^6$ is at each occurrence independently hydrogen, halo, C$_1$-C$_6$alkyl, C$_1$-C$_6$alkoxy, —CF$_3$, —CN or —NO$_2$; and Ar is aryl.

In certain embodiments, the compound of Formula (IV) is racemic. In certain embodiments, the compound of Formula 4 is the (+)- or (−)-enantiomer.

In certain embodiments, provided herein are compounds of Formula (IV), wherein $R^1$ is —CH$_3$.

In certain embodiments, provided herein are compounds of Formula (IV), wherein $R^2$, $R^3$ and $R^6$ are each H and $R^4$ and $R^5$ are each C$_1$-C$_6$alkoxy.

In one embodiment, provided herein are compounds of Formula (IV), wherein R is —CH$_3$ and Ar is phenyl.

In certain embodiments, provided herein are compounds of Formula (IV), wherein R is C$_1$-C$_6$alkyl; $R^1$ is C$_1$-C$_6$alkyl; $R^2$ is H; $R^3$ is H; $R^4$ is C$_1$-C$_6$alkoxy; $R^5$ is C$_1$-C$_6$alkoxy; and $R^6$ is H.

In certain embodiments, provided herein are compounds of Formula (IV), wherein R is —CH$_3$; $R^1$ is —CH$_3$; $R^2$ is H; $R^3$ is H; $R^4$ is —OCH$_3$; $R^5$ is —OCH$_2$CH$_3$; $R^6$ is H; and Ar is phenyl. In one embodiment, said compound is the hydrochloride salt. In one embodiment, said hydrochloride salt is the isopropanol solvate.

In one embodiment, the compound of Formula (IV) is:

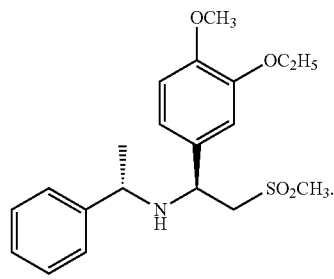 [SMILES: CCOc1cc([C@@H](CS(C)(=O)=O)N[C@@H](C)c2ccccc2)ccc1OC]

Particular embodiments provided herein are illustrated by the synthesis of the aminosulfone Compound B in the schemes above. Modifications of variables including, but not limited to, reaction solvents, reaction times, reaction temperatures, reagents, starting materials, and functional groups in the particular embodiments of the synthesis of Compound B will be apparent to those of ordinary skill in the art.

5. EXAMPLE

Example 1

Synthesis of (S)-1-(3-ethoxy-4-methoxyphenyl)-2-methanesulfonylethylamine (Compound B) via Scheme 1

In the first step, 3-Ethoxy-4-methoxy benzonitrile (100 g, 0.564 mol) was treated with the anion of dimethylsulfone (106.2 g, 1.128 mol, 2.0 eq), with n-BuLi (640 ml, 1.019 mol, 1.8 eq, 15% in n-Hexane solution) and in tetrahydrofuran (900 ml) as solvent to afford an enamine which, upon in situ hydrolysis with aqueous 2N hydrochloric acid (800 ml), afforded 1-(3-Ethoxy-4-methoxyphenyl)-2-methanesulfonyl ethanone (135-143 g) (Compound C), in 88-93% yield and with >98% chemical purity by HPLC.

In the second step, upon treatment of the keto derivative (100 g, 0.367 mol) Compound C with (S)-(−)-1-Phenylethylamine (150 ml, 1.165 mol, 3.17 eq) in toluene (500 ml) as solvent with catalytic para-toluenesulfonic acid (14.0 g, 0.073 mol, 0.2 eq) and removal of water by Dean-Stark distillation, an intermediate imine was formed, which was treated, without isolation, with sodium borohydride (20.8 g, 0.551 mol, 1.5 eq) in acidic medium followed by hydrolysis of the resulting borate with aqueous sodium hydroxide or hydrochloric acid, to afford the chiral N-benzylated derivative of aminosulfone, [1-(3-Ethoxy-4-methoxyphenyl)-2-methanesulfonyl ethyl]-(1-phenylethyl)amine (Compound D). This product was isolated as the isopropanol solvate of its hydrochloride salt to afford pure product (137-141 g) in 79-81% yield over two steps, with >99% chemical purity and >99% chiral purity. Enamine formation can also be accomplished using the strong Lewis acid Ti(OEt)$_4$ in tetrahydrofuran as solvent.

Finally, the N-benzylated aminosulfone derivative Compound D (100 g, 0.211 mol) was hydrogenated with 5% Pd/C (5.0 g), in methanol solvent (1000 ml) and at room temperature, to afford the pure S-aminosulfone Compound B (49-54 g) with 86-94% yield and >99% chiral and chemical purity.

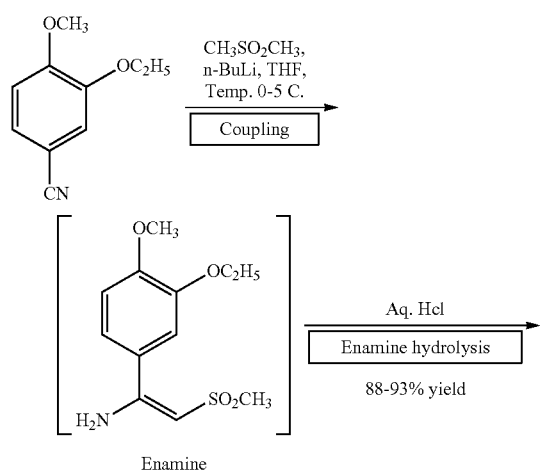

Data for 1-(3-ethoxy-4-methoxyphenyl)-2-methanesulfonylethanone (Compound C)

The compound is a white solid; M R (° C.) 140.1-142.0; ESI MS: 271.3 [M−1].

IR (cm$^{-1}$) 3448.8, 3325.7, 2977.1, 2929.3, 1671.9, 1594.0, 1580.0, 1522.7, 1405.1, 1343.2, 1270.1, 1248.2, 1207.2, 1179.8, 1162.1, 1124.5, 1041.0, 1015.0, 961.1, 949.1, 825.1, 804.7, 777.7.

$^1$H NMR (CDCl$_3$, 400 MHz) δ 1.48 (t, J=7.0 Hz, 3H), 3.13 (s, 3H), 3.95 (s, 3H), 4.15 (q, J=7.0 Hz, 2H), 4.55 (s, 2H), 6.93 (d, J=8.4 Hz, 1H), 7.52 (d, J=1.8 Hz, 1H), 7.60 (dd, J=1.9 Hz, J=8.4 Hz, 1H).

$^{13}$C NMR (CDCl$_3$, 100 MHz) δ 14.6, 41.7, 56.2, 61.0, 64.4, 110.3, 111.6, 124.8, 128.7, 148.6, 154.9, 187.5.

Data for (1S,1'S)-[1-(3-Ethoxy-4-methoxyphenyl)-2-methanesulfonyl]ethyl-N-(1'-phenylethyl)amine (Compound D)

The compound is a white solid; M R (° C.) 143.8-147.3; ESI MS: 378.2 [M+1].

IR (cm$^{-1}$) 3297.2, 2981.3, 2941.0, 2629.5, 2463.6, 1595.7, 1520.0, 1456.7, 1442.5, 1304.6, 1266.5, 1147.1, 1133.0, 1028.9, 945.9, 873.1, 762.6, 702.9.

$^1$H NMR (CDCl$_3$, 400 MHz) δ 1.14 (d, J=6.0 Hz, 6H), 1.43 (t, J=7.0 Hz, 3H), 1.60 (d, J=6.8 Hz, 3H), 2.20 (bs, 1H), 2.27 (s, 3H), 3.84 (s, 3H), 3.93-3.96 (m, 1H), 4.01-4.02 (m, 1H), 4.06-4.13 (m, 3H), 4.47 (m, 1H), 4.65 (m, 1H), 6.82 (d, J=8.2 Hz, 1H), 7.08 (d, J=8.0 Hz, 1H), 7.22-7.27 (m, 3H), 7.33-7.35 (m, 3H), 9.86 (bs, 1H), 10.50 (bs, 1H).

$^{13}$C NMR (CDCl$_3$, 400 MHz) δ 14.6, 18.3, 25.2 (2C), 42.2, 55.8, 57.1, 57.4, 57.6, 64.2, 64.7, 111.3, 112.0, 122.2, 123.7, 128.1 (2C), 128.8 (2C), 129.1, 135.7, 149.2, 150.4.

Data for (S)-1-(3-Ethoxy-4-methoxyphenyl)-2-methanesulfonylethylamine (Compound B)

The compound is a white solid; M R (° C.) 107.6-108.7; ESI MS: 274.3 [M+1].

IR (cm$^{-1}$) 3390.8, 3321.0, 2973.0, 2933.6, 1590.9, 1523.9, 1478.3, 1448.5, 1435.4, 1396.1, 1328.8, 1267.3, 1247.5, 1137.2, 1048.9, 1024.7, 963.4, 777.7.

$^1$H NMR (CDCl$_3$, 400 MHz) δ 1.44 (t, J=7.0 Hz, 3H), 1.87 (bs, 2H), 2.88 (s, 3H), 3.20 (dd, J$_{1,2}$=3.0 Hz, J$_{1,3}$=14.0 Hz, 1H), 3.30 (dd, J$_{1,2}$=9.5 Hz, J$_{1,3}$=14.0 Hz, 1H), 3.83 (s, 3H), 4.08 (q, J=7.0 Hz, 2H), 4.55 (dd, J$_{1,2}$=3.0 Hz, J$_{13}$=9.5 Hz, 1H), 6.81-6.90 (m, 3H).

$^{13}$C NMR (CDCl$_3$, 100 MHz) δ 14.7, 42.3, 50.9, 55.9, 63.0, 64.3, 110.6, 111.5, 118.1, 135.5, 148.6, 148.9.

This route has been demonstrated on a 100 kg scale. Compound C and Compound D were previously unknown in the literature, and are novel intermediates used for the synthesis of (S)-Aminosulfone.

There was a 15% overall yield, which was improved to 45%, which is better than the 30% overall yield typically observed in the traditional process.

Example 2

Synthesis of (S)-1-(3-ethoxy-4-methoxyphenyl)-2-methanesulfonylethylamine (Compound B) via Scheme 2

In the first step, a reaction flask was charged with 3-ethoxy-4-methoxybenzaldehyde (2.0 g, 11 mmol), (R)-tert-butylsulfinamide (Ellman's auxiliary) (1.5 g, 12.2 mmol, 1.1 equiv) and THF (20 vol) then treated with Ti(OEt)$_4$ (4.6 mL, 22 mmol, 2.0 equiv, ~20% Ti). The reaction was heated for ~6 h at 65-67° C. then cooled to 20-25° C. and added to 2% aqueous NaCl (20 vol). The slurry was filtered and the white precipitate (titanium salts) was washed with EtOAc. The organic portion was dried with MgSO$_4$ and concentrated to afford (E)-N-(3-ethoxy-4-methoxybenzylidene)-2-methylpropane-2-sulfinamide (Compound E).

In the second step, a reaction flask was charged with Compound E (1.0 g, 3.5 mmol), AlMe$_3$ (1.9 mL, 3.9 mmol, 1.1 equiv) in THF (7 vol) then cooled to −78° C. A solution of Me$_2$SO$_2$ (0.4 g, 4.2 mmol, 1.2 equiv), n-BuLi (1.4 mL, 3.5 mmol, 1.0 equiv) in THF (3 vol) was added dropwise. The reaction mixture was stirred for 30 min then warmed to 20-25° C. and stirred for 3-4 h. 6N HCl in i-PrOH (1.0 ml, 1.2 equiv) was added followed by MTBE (10-15 mL) and then stirred for 12 h. The solid was collected via filtration and washed with MTBE to yield N-(1-(3-ethoxy-4-methoxyphenyl)-2-(methylsulfonyl)ethyl)-2-methylpropane-2-sulfinamide (Compound F).

Finally, a reaction flask was charged with Compound F in MeOH (10 vol) at 20-25° C. then treated with 2N HCl/Et$_2$O (~2 mL, 2.0 equiv) and stirred for 12 h. The reaction mixture was concentrated to dryness and the resulting solid was dissolved in water/EtOAc. The aqueous portion was neutralized then extracted with CH$_2$Cl$_2$. The combined organic layers were dried with MgSO$_4$ then concentrated to provide (S)-1-(3-ethoxy-4-methoxyphenyl)-2-methanesulfonylethylamine (Compound B).

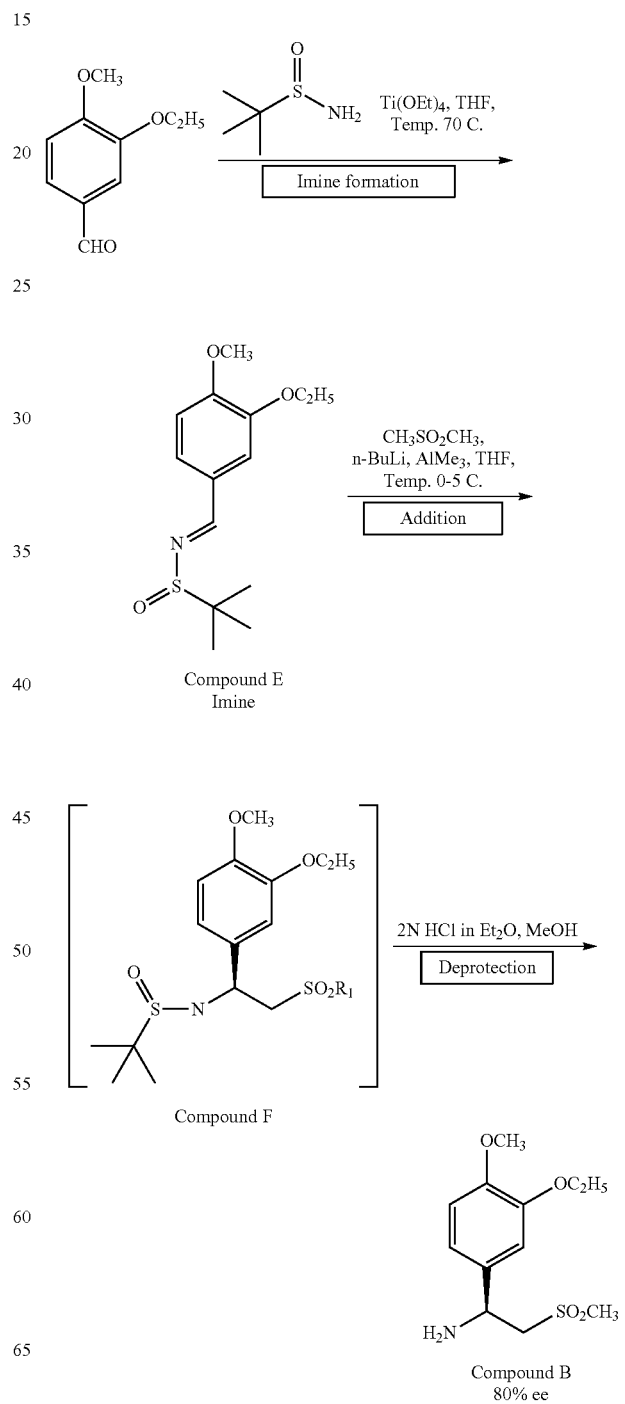

Data for (E)-N-(3-ethoxy-4-methoxybenzylidene)-2-methylpropane-2-sulfinamide (Compound E)

HPLC Parameters: Aquity UPLC C18, 2.1×150 mm, 1.7 μm, 10:90 to 90:10, CH$_3$CN: 0.1% H$_3$PO$_4$ water, 35° C., 0.85 mL/min, 240 nm, 98% area. $^1$H NMR DMSO-d$_6$: δ 8.4 (s, 1H), 7.5 (m, 2H), 7.1 (d, 1H, J=9 Hz,), 4.07 (q, 2H, J=6 Hz), 3.9 (s, 3H), 1.4 (t, J=6 Hz), 1.2 (s, 9H).

Data for (E)-N-(3-ethoxy-4-methoxybenzylidene)-2-methylpropane-2-sulfinamide (Compound F)

LC/MS ES$^+$ (M+1) 378; HPLC Parameters: Aquity UPLC C18, 2.1×150 mm, 1.7 μm, 10:90 to 90:10, CH$_3$CN: 0.1% H$_3$PO$_4$ water, 35° C., 0.85 mL/min, 240 nm, >98% area.

Data for (S)-1-(3-ethoxy-4-methoxyphenyl)-2-methanesulfonylethylamine (Compound B)

HPLC Parameters: Aquity UPLC C18, 2.1×150 mm, 1.7 μm, 10:90 to 90:10, CH$_3$CN: 0.1% H$_3$PO$_4$ water, 35° C., 0.85 mL/min, 240 nm, >89% area.
Chiral HPLC Parameters: ChiralPak AD, 250×4.6 mm, 10 μm, 55/45/0.1 v/v, heptanes/IPA/diethylamine, 25° C., 1 mL/min, 240 nm, R (10%), S (90%), 80% ee.
$^1$H NMR DMSO-d$_6$: δ 7.0 (s, 1H), 6.99-6.8 (d, 2H), 4.3-4.0 (m, 1H), 4.0 (q, 2H, J=6 Hz), 3.96 (s, 3H), 3.5-3.1 (m, 4H), 2.9 (s, 3H), 1.4 (t, 3H, J=6 Hz).

The processes described herein provide efficient, cost effective, commercially viable, environmentally friendly, and safe synthetic routes for the preparation of chiral aminosulfones, and avoid classical resolution to separate unwanted enantiomers from the racemic mixture, as is necessary in the traditional process. In particular, certain processes provided herein do not require any chiral separation to synthesize the chiral aminosulfone Compound B, eliminating the need to use chiral N-acetyl-L-leucine for chiral resolution. The ability to isolate the chirally pure target single enantiomer aminosulfone and to avoid forming the leucine salt in the downstream chemistry toward the compound Apremilast (i.e., eliminating the extra weight of unwanted N-acetyl-L-leucine and (R)-isomer) is an added advantage allowing for larger batch sizes within existing manufacturing facilities.

Processes provided herein circumvent the removal of the redundant enantiomer (e.g., the (R)-aminosulfone isomer following the separation of target (S)-aminosulfone Compound B). Processes provided herein are more efficient and environmentally friendly because there is no formation of the unwanted enantiomer, thus there is no need to treat or incinerate the unwanted isomer; accordingly, the yield and quality of the target isomer are improved, which is a green chemistry development. Due to improvement in the yield, productivity is increased with lesser time needed for operation.

What is claimed is:

1. A compound of Formula (IV):

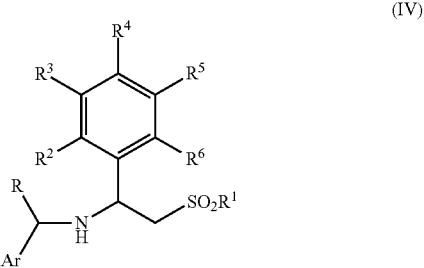

(IV)

or a pharmaceutically acceptable salt, hydrate, solvate, or polymorph thereof, wherein:
R is C$_1$-C$_6$alkyl;
R$^1$ is C$_1$-C$_6$alkyl;
each of R$^2$, R$^3$, R$^4$, R$^5$, and R$^6$ is at each occurrence independently hydrogen, halo, C$_1$-C$_6$alkyl, C$_1$-C$_6$alkoxy, —CF$_3$, —CN or —NO$_2$; and
Ar is aryl.

2. The compound of claim 1, wherein the compound of Formula (IV) is racemic.

3. The compound of claim 1, wherein the compound of Formula (IV) is the (+)- or (−)-enantiomer.

4. The compound of claim 1, wherein R is —CH$_3$; R$^1$ is —CH$_3$; R$^2$ is H; R$^3$ is H; R$^4$ is —OCH$_3$; R$^5$ is —OCH$_2$CH$_3$; R$^6$ is H; and Ar is phenyl.

5. The compound of claim 4, wherein the compound is the hydrochloride salt.

6. The compound of claim 4, wherein the compound is the isopropanol solvate hydrochloride salt.

7. The compound of claim 1, wherein the compound is:

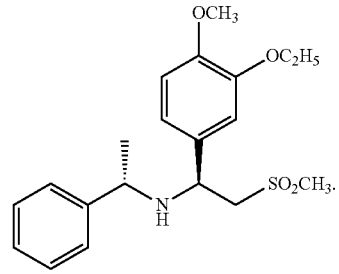 [SMILES: CCOc1cc([C@@H](CS(C)(=O)=O)N[C@@H](C)c2ccccc2)ccc1OC]

8. The compound of claim 7, wherein the compound is the hydrochloride salt.

9. The compound of claim 7, wherein the compound is the isopropanol solvate hydrochloride salt.

* * * * *